(12) United States Patent
Färber

(10) Patent No.: US 7,416,409 B2
(45) Date of Patent: Aug. 26, 2008

(54) DEVICE FOR ADJUSTING TOOTH AND/OR JAW MALPOSITIONS

(76) Inventor: Klaus-Erich Färber, Fliederweg 14, Lemgo (DE) 32657

( * ) Notice: Subject to any disclaimer, the term of this patent is extended or adjusted under 35 U.S.C. 154(b) by 0 days.

(21) Appl. No.: 10/570,740

(22) PCT Filed: Sep. 9, 2004

(86) PCT No.: PCT/DE2004/002017

§ 371 (c)(1),
(2), (4) Date: Jun. 7, 2006

(87) PCT Pub. No.: WO2005/023136

PCT Pub. Date: Mar. 17, 2005

(65) Prior Publication Data

US 2007/0026357 A1   Feb. 1, 2007

(30) Foreign Application Priority Data

Sep. 9, 2003   (DE)   ............... 103 41 423

(51) Int. Cl.
*A61D 5/00*   (2006.01)
(52) U.S. Cl. ........................ 433/18; 433/19
(58) Field of Classification Search .......... 433/5–7, 433/17–19, 21–24
See application file for complete search history.

(56) References Cited

U.S. PATENT DOCUMENTS

| | | | | |
|---|---|---|---|---|
| 3,798,773 A * | 3/1974 | Northcutt | ............ | 433/19 |
| 4,462,800 A * | 7/1984 | Jones | ............ | 433/19 |
| 4,551,095 A * | 11/1985 | Mason | ............ | 433/19 |
| 4,708,646 A * | 11/1987 | Jasper | ............ | 433/19 |
| 5,435,721 A * | 7/1995 | Vogt | ............ | 433/19 |
| 5,897,313 A * | 4/1999 | Cleary et al. | ............ | 433/19 |
| 6,053,730 A * | 4/2000 | Cleary | ............ | 433/19 |
| 2002/0031741 A1* | 3/2002 | Williams | ............ | 433/19 |
| 2002/0132207 A1* | 9/2002 | Tuneberg | ............ | 433/19 |

OTHER PUBLICATIONS

International Search Report dated Feb. 24, 2005 issued for the underlying International Application No. PCT/DE2004/002017.

* cited by examiner

*Primary Examiner*—Cris L. Rodriguez
*Assistant Examiner*—Sunil K Singh
(74) *Attorney, Agent, or Firm*—Cohen Pontani Lieberman & Pavane LLP

(57) ABSTRACT

An appliance for adjusting tooth and/or jaw malpositions, includes an upper arch wire suitably to be attached to teeth on the upper jaw of a user; a lower arch wire suitably to be attached to teeth on the lower jaw of the user; and a force-transfer element for mechanically connecting the upper arch wire and the lower arch wire to each other. The force-transfer element has a first longitudinal axis and includes a first end comprising an angled section. The angled section has a first hole, the longitudinal axis of which is parallel to the first longitudinal axis. The force-transfer element also includes a second end which is opposite to the first end and has a second hole which is rotationally offset 90° relative to the first hole.

17 Claims, 4 Drawing Sheets

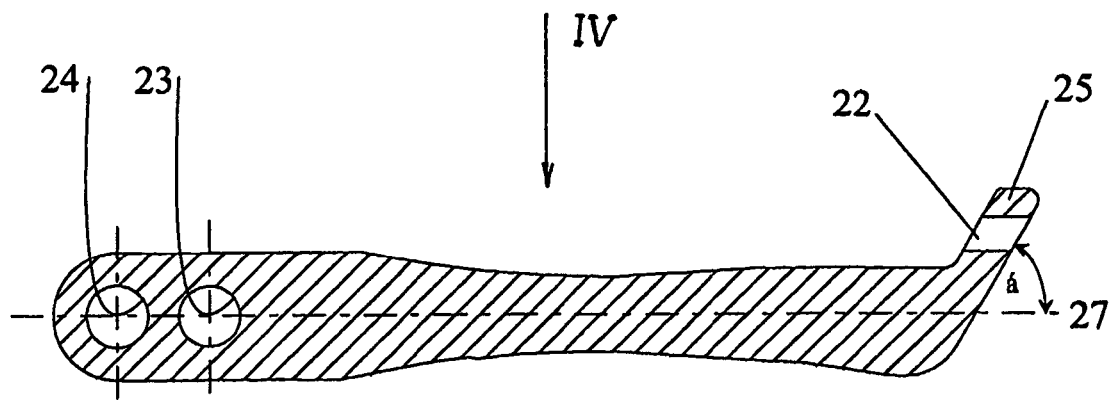
Fig. 3
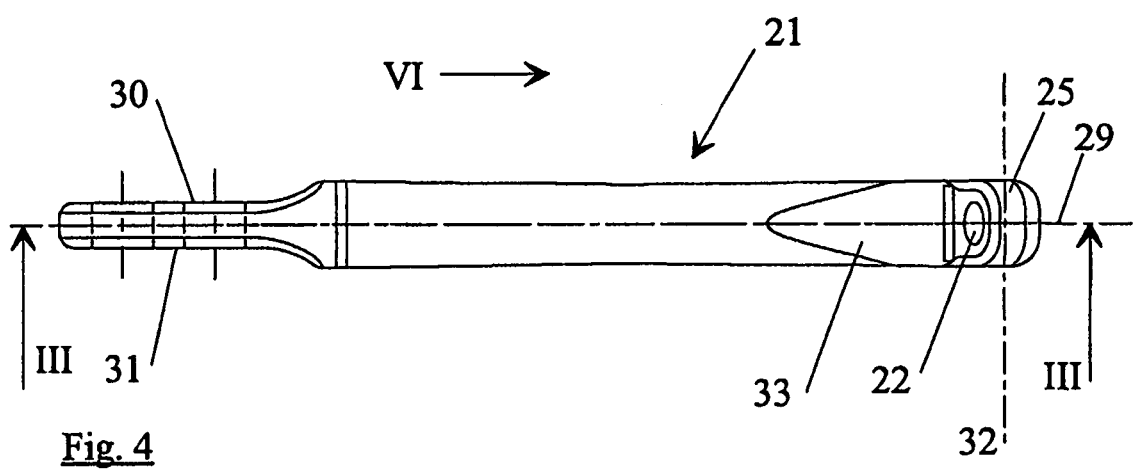
Fig. 4
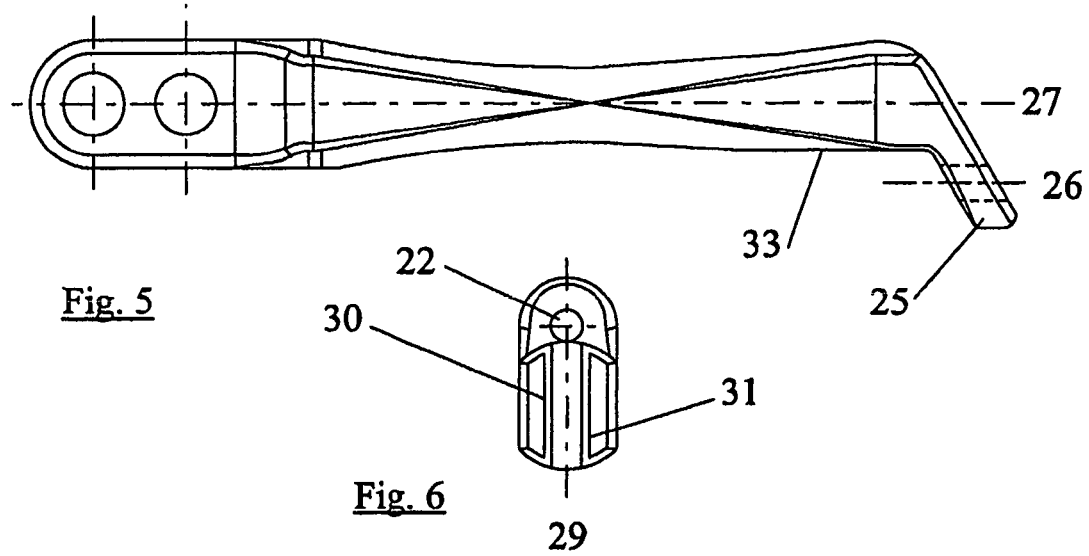
Fig. 5
Fig. 6

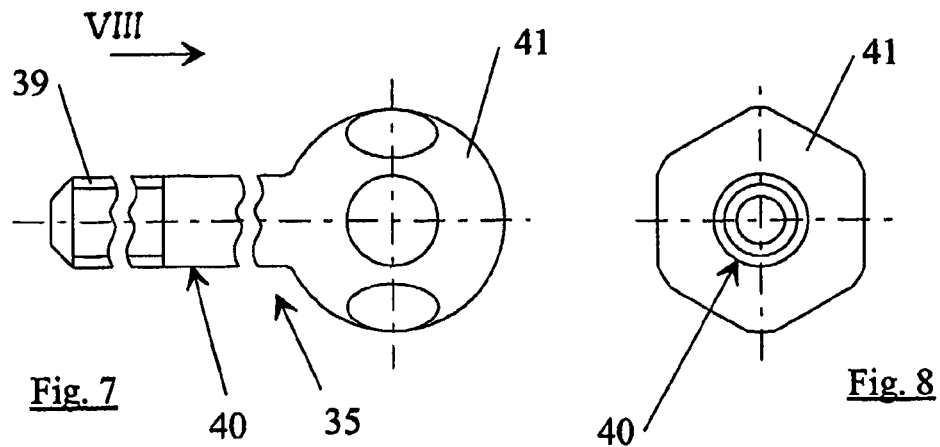
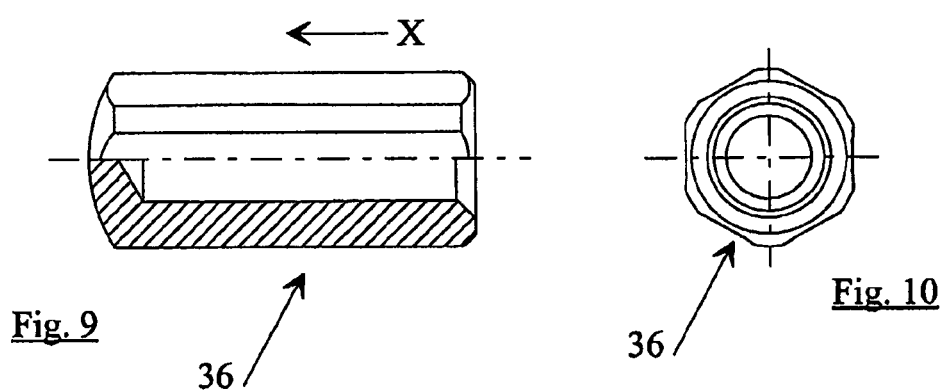
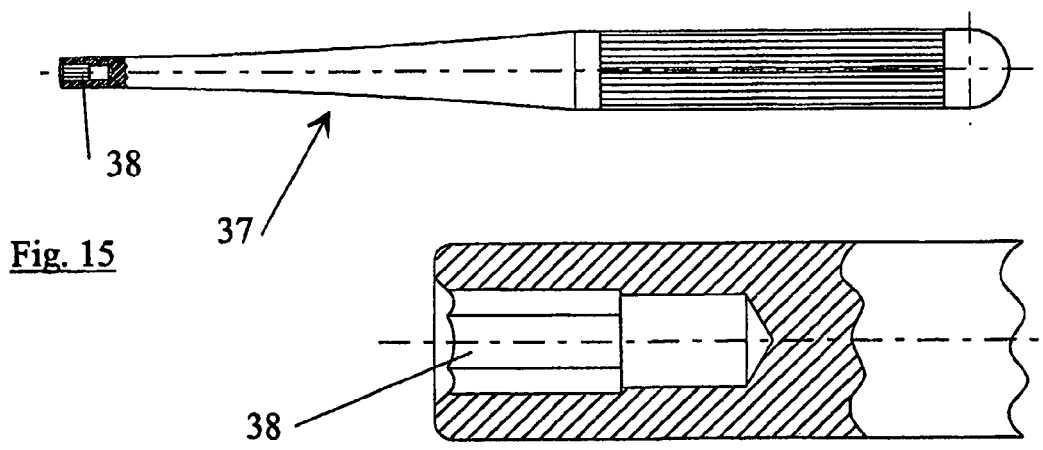

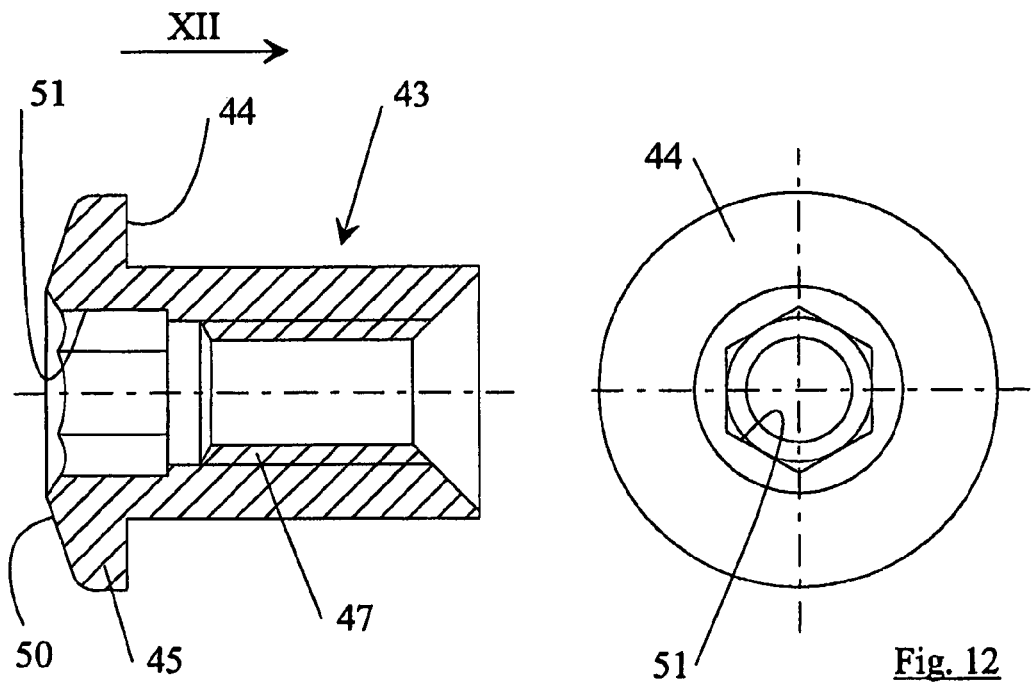
Fig. 11      Fig. 12
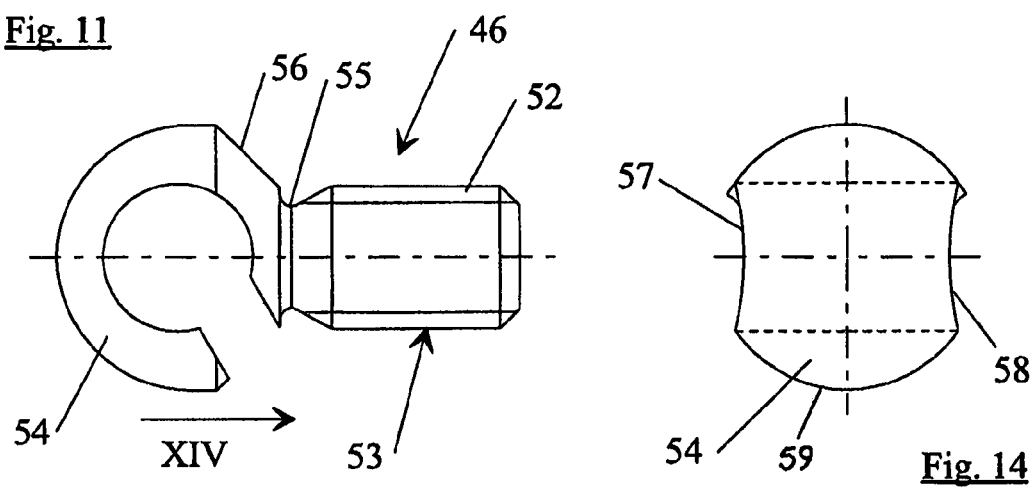
Fig. 13      Fig. 14
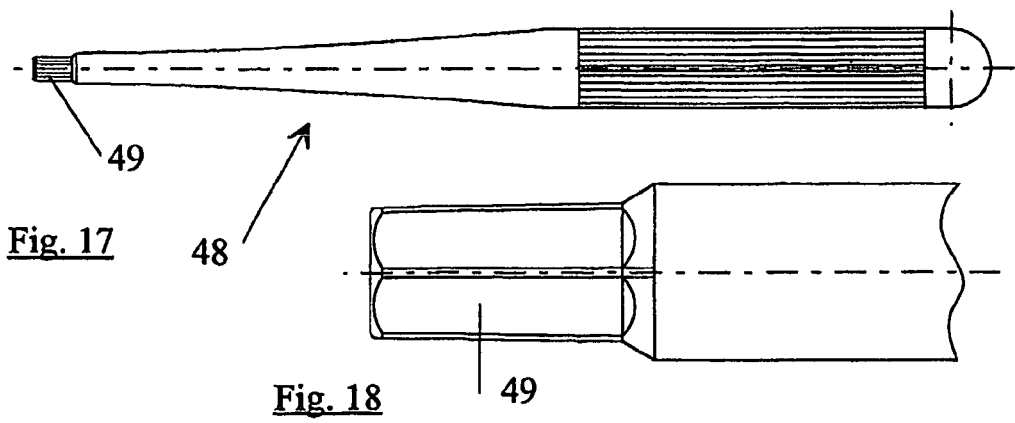
Fig. 17
Fig. 18

DEVICE FOR ADJUSTING TOOTH AND/OR JAW MALPOSITIONS

CROSS-REFERENCE TO RELATED APPLICATIONS

This is a U.S. national stage of application No. PCT/DE2004/002017, filed on 9 Sep. 2004. Priority is claimed on German Application No. 103 41 423.1, filed on 9 Sep. 2003.

BACKGROUND OF THE INVENTION

1. Field of the Invention

The invention pertains to an appliance for correcting tooth and/or jaw malpositions, with an upper and a lower arch wire, which are attached to the teeth and which are connected mechanically to each other by at least one force-transfer element, usually by two force-transfer elements.

2. Description of the Related Art

The advantages of tooth-mounted appliances for correcting malpositions of the teeth and/or jaws have been recognized by orthodontists and dentists for many years. The mechanical connection of the upper jaw to the lower jaw to improve the occlusion, however, still represents a problem. There are only four possible ways to connect the upper and lower jaws together.

First, a distinction must be made between a rigid and a flexible connection. In addition, the jaws can be either moved toward each other, i.e., by exerting pulling forces on them, or they can be moved away from each other, i.e., by exerting pushing forces on them. These possibilities lead to the various appliances for mechanically connecting the jaws. Although no rigid pulling applications are known, elastic pulling applications can be designed with the help of elastic bands or springs. An example of a rigid pushing application is Herbst's hinge. A flexible pushing application is known in the form of the so-called "Jasper jumper", described in U.S. Pat. No. 4,708,646.

The known appliances are of complicated design and usually have bulky, bent compression springs, of which a very wide variety must be kept on hand to fulfill all the necessary functions. In particular, a progressive jaw correction requires the use of a series of new components to fit the changing size of the jaws.

SUMMARY OF THE INVENTION

Against this background, the invention has the task of providing an appliance of the type in question which produces intermaxillary changes very quickly, but which exerts only slight, adjustable, and continuous forces, by means of which the teeth can be shifted, either individually or in larger groups, to achieve significant dento-alveolar changes. As a result, the bite position is changed and a correct anterior-posterior positional relationship can be obtained. In particular, as a function of the actual treatment case in question, it is to be possible to transmit between the jaws either headgear-like forces or activator-like forces or a combination of the two.

To produce a headgear-like effect, the arch wire for the lower jaw must first be prepared to serve as the anchoring unit. This is usually done by adding a large square bend to the anterior lingual crown torque (anterior buccal root torque) and by providing tie-bag bends in front of the first molars.

The second molars should also be banded, and it is necessary to provide tie-bag bends on both sides. That is, the arch wire should be anchored or tied back by ligatures in the area of the molars.

To achieve the activator effect, both the lower and the upper dental arch are blocked by the use of appropriate square wires and torque bends. As soon as the force-transfer element is inserted, the patient is advised not to fight the forward-directed pressure on the lower jaw but rather to allow the lower jaw to be pushed forward into the position of a class I occlusion. Then there is only a relatively weak force acting on the teeth, and the developing functional matrix receives the opportunity to normalize its growth. The transfer element holds the position of the lower jaw and the relationship of the teeth in the desired position, thus allowing natural growth and the remodulation of the mandibular joint and the mandibular musculature to proceed in such a way that the desired positional relationship of the lower jaw with respect to the upper jaw is promoted.

In an appliance for the correction of tooth and/or jaw malpositions with an upper and a lower arch wire, each of which is securely connected to the teeth, these arch wires being mechanically connected to each other by at least one force-transfer element, the technical problem explained above is solved by the measure that the force-transfer element is designed as a solid, flat, bar-like jumper, and that at least two holes, rotationally offset 90° from each other, are provided at the long ends of the jumper, the first hole being introduced into a angled section, the longitudinal axis of this first hole being parallel to the longitudinal axis of the jumper.

The appliance according to the invention offers several advantages. The design of the force-transfer element as a solid, flat, bar-like jumper, produced out of plastic, for example, by injection-molding or casting, significantly lowers the cost of the appliance and simplifies the correction of malpositioned teeth or jaws.

In particular, only a single type of jumper will usually be sufficient to correct a malpositioned tooth and/or jaw, for which reason it is no longer necessary to maintain a large inventory of appliances.

This means that, when the appliance according to the invention is used, the same type of jumper can be used as the force-transfer element on both sides of the jaw for any required length.

This is made possible essentially by the presence of the minimum of two holes, which are rotationally offset from each other by 90° and which serve to attach the jumper to the two arch wires. Following the shape of the jaw, the two holes are rotated 90° from each other, the first hole being introduced into an angled section. The longitudinal axis of this hole is parallel to the longitudinal axis of the jumper, so that the jaw extends between these two holes.

It is obvious that all the edges of the jumper are rounded to prevent any possible injury to the gums. In addition, for hygienic reasons, a high-quality plastic, especially a plastic with elastic properties, should be used.

It has also been found advisable in practice for the end of the jumper opposite the angled section to have narrower cross section and to be provided with two holes, one next to the other in the longitudinal direction of the jumper. In particular, the two holes are next to each other on the longitudinal axis of the jumper. With the help of a few different elements for fastening the jumper to the arch wires, the design of the jumper therefore makes it possible to handle basically two different adjustment lengths.

The distance between the rotationally offset holes should be between 30 mm and 40 mm, and preferably between 34 mm and 38 mm. If two holes are provided next to each other at one end of the jumper in the longitudinal direction of the jumper, the inner hole will be the shorter of the two distances indicated above from the hole in the angled section, the outer hole the longer of the two distances away from it.

The angled section forms an angle of approximately 60° with the longitudinal axis of the jumper and is dimensioned in such a way that there is a vertical offset of 3-5 mm, and especially of 3.5 mm, between this hole and the hole or holes at the other end, this offset preferably being measured between the longitudinal axis of the jumper and the axis of the hole in the angled section.

The jumper is preferably symmetric to a longitudinal center plane, as a result of which two similar jumpers can be used to connect the arch wires. When the jumper is in use, the longitudinal center plane will be parallel to the teeth or to the jaws. It is therefore not necessary to adapt the appliance specifically to the left or to the right side of the jaw.

In the appliance according to the invention, it is also provided that the angled section of the jumper is held in place on the upper arch wire, preferably by means of a screw. As a result, a comparatively rigid fixation of the jumper on the upper jaw is obtained, especially when a fastening element is present which is attached to the tooth.

A fastening element of this type, attached to the tooth, can carry a headgear tube, to which the jumper can be effectively attached. In a case such as this, it is provided that the screw, designed as a ball-head screw, first passes through the first hole in the angled section of the jumper and then passes through the headgear tube, which is attached to the arch wire. The screw is finally secured to the headgear tube by a cap nut. The jumper can therefore be very easily replaced, and its attachment can also be very easily adjusted.

In particular, the length of the shaft of the screw is calculated so that a distance of 3-10 mm, and especially a distance of 4-8 mm, remains between the head of the screw and the headgear tube. Preferably only two different screws are provided for a treatment. The length of the shaft is calculated so that a distance of 4 mm remains between the head of the one screw and the headgear tube, and a distance of 8 mm remains between the head of the other screw and the headgear tube. The position of the jaw or tooth is therefore not corrected in a continuous fashion but rather in two stages, which is not a problem.

In a further elaboration of the appliance according to the invention, a bushing with an internal thread in one end is inserted into a hole in the end of the jumper opposite the angled section. The other end of the bushing has a flange, the ring-shaped shoulder of which rests on a flat side of the jumper. In addition, an open screw hook is screwed into the internal thread; this hook fits over a section of the lower arch wire. This makes it possible to attach the jumper to the lower jaw arch wire very easily, and the attachment can also be very easily adjusted. The positioning and/or fixation of the hook is achieved by relative rotation of the screw hook in the internal thread of the bushing.

It has also been found to be advantageous for the bushing to be inserted into the hole so that it can be turned and for the bushing to be turned by means of a turning tool, for which purpose this bushing has a socket in the end opposite the inserted screw hook, especially in the form of a smooth polygonal socket, designed to accept the turning tool. As a result of this measure, it is not necessary to disengage the screw hook from the section of the lower arch wire when it is desired to adjust the jumper.

BRIEF DESCRIPTION OF THE DRAWINGS

The invention is explained in greater detail on the basis of the drawings, which show a treatment method and an exemplary embodiment in schematic fashion:

FIG. 3 shows a central longitudinal cross section through the jumper along line III-III of FIG. 4;

FIG. 4 shows a plan view of the jumper according to the arrow IV in FIG. 3;

FIG. 5 shows a side view of the jumper;

FIG. 6 shows a view according to the arrow VI in FIG. 4;

FIG. 7 shows a ball head screw for attaching the jumper;

FIG. 8 shows a view according to the arrow VIII in FIG. 7;

FIG. 9 shows a partial cross section through a cap nut for holding the ball head screw in place;

FIG. 10 shows a view according to the arrow X in FIG. 9;

FIG. 11 shows a bushing, which can be inserted into a hole;

FIG. 12 shows a view in the direction of arrow XII in FIG. 11;

FIG. 13 shows a screw hook;

FIG. 14 shows a view of the screw hook according to the arrow XIV in FIG. 13;

FIG. 15 shows a first tool, for the sake of completeness;

FIG. 16 shows an enlarged view of the socket in the tool according to FIG. 15;

FIG. 17 shows a second tool; and

FIG. 18 shows an enlarged view of the screw-driving tip of the tool according to FIG. 17.

DETAILED DESCRIPTION OF THE PRESENTLY PREFERRED EMBODIMENT

Figure 1:
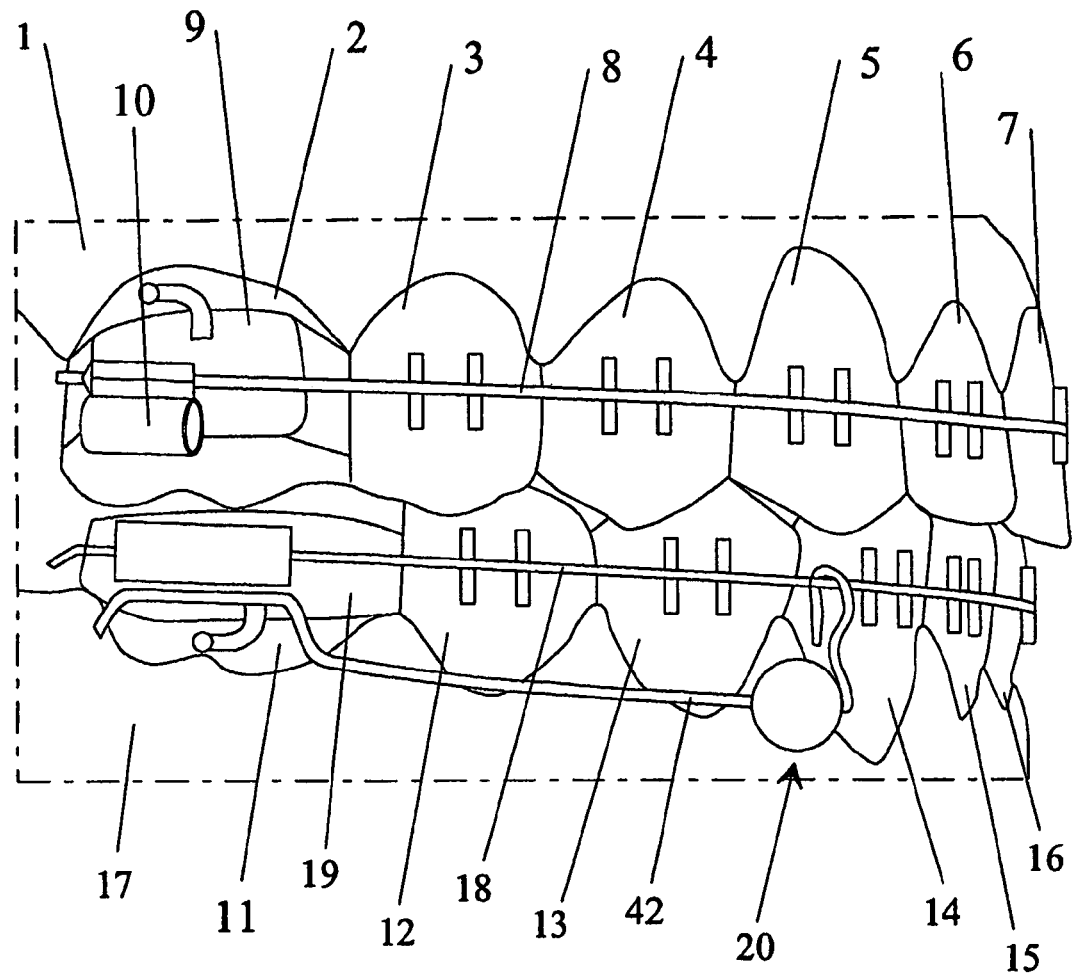
FIG. 1 shows an appliance according to the invention for the correction of malpositioned teeth or jaws without a force-transfer element.

FIG. 1 is a simplified schematic diagram of an appliance according to the invention for correcting tooth and/or jaw malpositions.

An upper arch wire 8 is firmly anchored to an upper jaw 1 by means of the visible teeth 2-7. Tooth 2 on the left in FIG. 1 carries a fastening element 9, connected in the conventional manner to tooth 2 for correction. This fastening element 9 is connected securely in turn to a headgear tube 10.

Teeth 11-16 of the lower jaw 17 are also connected securely to an arch wire 18, where the tooth 11, in the present exemplary embodiment, is provided with a fastening element 19 with a ball stop 20.

Figure 2:
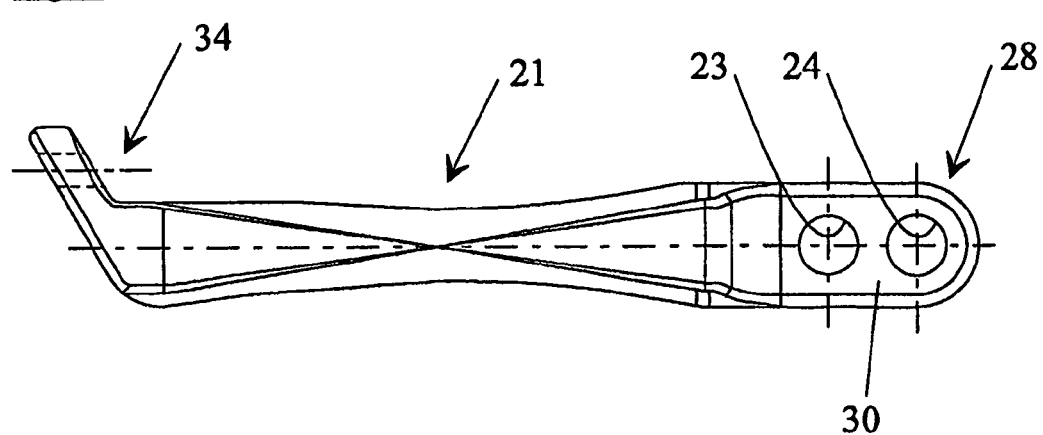
FIG. 2 shows a force-transfer element in the correct position with respect to its longitudinal orientation.

The mechanical connection between the upper jaw 1 and the lower jaw 17 by way of the arch wires 8 and 18, attached to teeth 2-7 and 11-16, respectively, is accomplished here by means of a jumper 21, shown in FIG. 2 underneath FIG. 1 in a position which is more-or-less correct for installation between the left mesial end of the headgear tube 10 and the distal side of the ball stop 20.

Other installation positions, especially also an attachment of the jumper 21 directly to the lower arch wire 18, are also possible. The type of attachment will usually be determined by the type of malposition to be corrected.

The jumper 21 according to FIGS. 2-6 is a one-piece part of elastic plastic, produced by casting or injection-molding. At its long ends the jumper 21 has holes 22, 23, 24, which are rotationally offset from each other by 90°. That is, the hole 22 is located in an angled section 25 in such a way that its longitudinal axis 26 is parallel to the longitudinal axis 27 of the jumper 21.

In the exemplary embodiment of the jumper 21, the two holes 23, 24 at the end 28 opposite the angled section 25 are located next to each other on the longitudinal axis 27 of the jumper 21. In the area of the holes 23, 24, the cross section of the jumper 21 tapers down toward the center longitudinal plane 29. Two parallel flat sides 30, 31 are thus formed, through which the holes 23, 24 are introduced in perpendicular fashion.

The distance between the axial center 32 of the hole 22 and one of the other holes should be in the range of 30-40 mm, and especially in the range of 34-38 mm. If, as in the present exemplary embodiment of the jumper 21, two holes 23, 24 are provided, the distance between the axial center 32 of the hole 22 and the axis of the nearer hole 23 is 34 mm, and the distance between the center 32 of the hole 22 and the axis of the farther hole 24 is 38 mm.

In the present exemplary embodiment of the jumper 21, the vertical offset between the two holes 23, 24 at the one end and the hole 22 at the other corresponds to the distance between the longitudinal axes 26, 27 and is preferably on the order of 3.5 mm, thus between 3 mm and 5 mm.

The angled section 25 is designed with this offset in mind. The angled section 25 forms an angle of α=60° with the longitudinal axis 27 of the jumper 21.

With the exception of the angled section 25 and a flattened area 33 in front of this angled section 25, the jumper 21 is symmetric with respect to a plane which passes through the longitudinal axis 27 and is perpendicular to the plane of FIG. 5. The symmetry with respect to the center longitudinal plane 29 is complete.

The end 34 of the jumper 21 with the angled section 25 is attached to the headgear tube 10 by means of the ball-head screw 35 shown in FIGS. 7 and 8 and by means of a cap nut 36 according to FIGS. 9 and 10.

The ball-head screw 35 has a shaft 40, part of which carries a thread 39. The shaft passes first through the hole 22 in the jumper 21 and then through the headgear tube 10, starting from the left in FIG. 1. The screw is then held in place from the right against the headgear tube 10 by the cap nut 36.

The cap nut 36 is turned from the front to perform the adjustments in the pharyngeal or oral cavity. For this purpose, the tool 37 shown in FIG. 15 is provided. This tool has a socket 38 designed to fit over the cap nut 36.

The length of the shaft 40 of the ball-head screw 35 is calculated so that a distance of 3-10 mm, and especially of 4-8 mm, remains between the head 41 of the screw and the headgear tube 10. The preferred approach is to provide only two screws 35, the lengths of their shafts being selected so that, in one case, a distance of 4 mm remains between the head 41 of the screw and the headgear tube 10 and, in the other case, a distance of 8 mm.

The holes 23, 24 in the jumper 21 are used to attach the jumper to the lower jaw 17. To determine which of the two holes, 22 or 23, is to be used, the jaws 1, 17 are brought into a centered relationship and held in place while the distance is measured between the mesial end of the headgear tube 10 and the distal side of the ball stop 20. For the given dimensions, an additional 12 mm is to be added to this measured length, this value being the sum of 4 mm for the length of the headgear tube, 4 mm for play, and the 4 mm required for activation.

The length of the shaft of the ball-head screw 35 and the hole, i.e., either 23 or 24, are selected in correspondence with this predetermined length.

So that the jumper 21 can be attached to a section 42 of the ball stop 20, a bushing 43 according to FIGS. 11 and 12 is pushed into one of the holes 23, 24 from the flat side 30 visible in FIG. 2 until a ring-shaped shoulder 44 of a flange 45 rests on this flat side 30. From the other side, a screw hook 46 according to FIGS. 13 and 14 is screwed into an internal thread 47 in the bushing 43. An Allen wrench 48 as a turning tool, comparable to the tool 37 but with an external wrench geometry at the turning tip 49, is used to make the adjustments here, for which purpose the end 50 of the bushing 43 opposite the screw hook 46 has a polygonal socket 51. As a result of this measure, it is possible to make adjustments from the outside, without the need to detach the screw hook 46 from the section 42.

In order to be screwed to the bushing 43, the screw hook 46 has a shaft 53 with a thread 52. As FIG. 14 also shows, an open hook 54, which is wider than the shaft 53 itself, is connected to one end of the shaft 53. Between the shaft 53 and the hook 54 are a comparatively deep groove 55 and a long bevel 56. A considerable flattened area 57 is provided on the end surface of the hook 54. Rounded areas 58, 59 on the hook 54, furthermore, allow it to rest securely against, for example, the ball stop 20.

With an appliance according to the invention, only a few components make it possible to achieve many different forms of mechanical connection between an upper jaw 1 and a lower jaw 17. It should also be obvious that these components are characterized by high surface quality and an accurate fit.

What is claimed is:

1. An appliance for correcting tooth or jaw malposition, comprising:
    an upper arch wire shaped to be attached to teeth on an upper jaw of a user;
    a lower arch wire shaped to be attached to teeth on a lower jaw of the user; and
    a force-transfer element for mechanically connecting the upper arch wire and the lower arch wire to each other, the force-transfer element being only a single solid one-piece bar element having a first longitudinal axis and comprising:
    a first end comprising an angled section, the angled section having a first hole, the first hole having a second longitudinal axis which is parallel to the first longitudinal axis;
    a second end opposite to the first end, the second end having at least a second hole which is rotationally offset 90° relative to the first hole; and
    an open screw hook and a bushing, the open screw hook having an open hook and a threaded shaft attached to the hook, the bushing having a first end having an internal thread, and a second end having a flange with a ring-shaped shoulder, wherein the bushing is inserted into the second hole with the ring-shaped shoulder resting against a flat side of the force-transfer element, and wherein the open screw hook is connected to the bushing with the threaded shaft being screwed into the internal thread of the bushing and the open hook engaging a section of the lower arch wire.

2. The appliance of claim 1, wherein the threaded shaft of the open screw hook having an end which is opposite to the hook and has a socket for receiving a driving tip of a turning tool.

3. The appliance of claim 1, wherein the force-transfer element is flat bar-shaped.

4. The appliance of claim 1, wherein the force-transfer element is made of elastic plastic.

5. The appliance of claim 1, wherein the second end has a reduced cross section, the second hole and a third hole being in the reduced cross section and adjacent to each other in a direction of the first longitudinal axis.

6. The appliance of claim 1, wherein the second end has a third hole, the second hole and the third hole being adjacent to each other on the first longitudinal axis.

7. The appliance of claim 1, wherein the distance between the first hole and the second hole is in the range of 30 to 40 mm.

8. The appliance of claim 5, wherein the distance between the first hole and the second hole is 34 mm, and the distance between the first hole and the third hole is 38 mm.

9. The appliance of claim 1, wherein the angled section forms an angle of 60° relative to the first longitudinal axis.

10. The appliance of claim 1, wherein the angled section is sized so that there is a vertical offset of 3 to 5 mm between the first longitudinal axis and the second longitudinal axis.

11. The appliance of claim 1, wherein the second hole has a third longitudinal axis, wherein the force-transfer element is symmetric to a longitudinal center plane which passes through the first longitudinal axis and is perpendicular to the third longitudinal axis, and wherein an additional force-transfer element is used for mechanically connecting the upper arch wire and the lower arch wire to each other.

12. The appliance of claim 1, wherein the angled section is connected to the upper arch wire.

13. The appliance of claim 12, wherein the angled section is connected to the upper arch wire by a screw.

14. The appliance of claim 13, further comprising a headgear tube attached to the upper arch wire, wherein the screw is a ball-head screw which passes first through the first hole and then through the headgear tube, and is finally locked in place by a cap nut.

15. The appliance of claim 14, wherein the ball-head screw has a head and a shaft attached to the head, and wherein the shaft has a length so that a distance of 3 to 10 mm remains between the head and the headgear tube.

16. The appliance of claim 15, wherein the shaft has a length so that a distance of 4 mm remains between the head and the headgear tube.

17. The appliance of claim 15, wherein the shaft has a length so that a distance of 8 mm remains between the head and the headgear tube.

\* \* \* \* \*